(12) United States Patent
Moore

(10) Patent No.: US 9,415,214 B2
(45) Date of Patent: Aug. 16, 2016

(54) METHOD AND DEVICE FOR REDUCING MUSCLE TENSION THROUGH ELECTRICAL MANIPULATION

(71) Applicant: Terry William Burton Moore, Guelph (CA)

(72) Inventor: Terry William Burton Moore, Guelph (CA)

(*) Notice: Subject to any disclaimer, the term of this patent is extended or adjusted under 35 U.S.C. 154(b) by 218 days.

(21) Appl. No.: 14/135,169

(22) Filed: Dec. 19, 2013

(65) Prior Publication Data

US 2015/0174399 A1 Jun. 25, 2015

Related U.S. Application Data

(62) Division of application No. 12/563,658, filed on Sep. 21, 2009.

(60) Provisional application No. 61/098,578, filed on Sep. 19, 2008.

(51) Int. Cl.
*A61B 5/00* (2006.01)
*A61N 1/36* (2006.01)
*A61B 5/0488* (2006.01)
*A61N 1/04* (2006.01)

(52) U.S. Cl.
CPC .......... *A61N 1/36003* (2013.01); *A61B 5/0488* (2013.01); *A61N 1/0452* (2013.01); *A61N 1/36014* (2013.01)

(58) Field of Classification Search
CPC ..... A61N 1/04; A61N 1/0404; A61N 1/0452; A61N 1/18; A61N 1/32
See application file for complete search history.

(56) References Cited

U.S. PATENT DOCUMENTS

| 4,838,272 | A  | * | 6/1989  | Lieber      | 607/48 |
| 6,865,423 | B2 | * | 3/2005  | Oldham      | 607/48 |
| 9,126,039 | B2 | * | 9/2015  | Fahey       |        |
| 9,149,386 | B2 | * | 10/2015 | Fahey et al.|        |

* cited by examiner

*Primary Examiner* — Max Hindenburg
(74) *Attorney, Agent, or Firm* — Daryl W. Schnurr

(57) ABSTRACT

A method and device for reducing muscle tension through electrical manipulation applies a low level current to muscles of a user. Each muscle has two electrodes applied thereto, one for passing the current from the device to the muscle, and the other for receiving the current from the muscle to complete the circuit. The device has several channels, one for each pair of electrodes, and current is passed through a muscle at a level below the threshold required to cause the muscle to contract. The device is programmed to automatically apply an alternating current at predetermined frequencies for predetermined time periods to each muscle of the user that is being treated. A method of diagnosing an ailment using the device is provided.

20 Claims, 3 Drawing Sheets

METHOD AND DEVICE FOR REDUCING MUSCLE TENSION THROUGH ELECTRICAL MANIPULATION

Applicant Claims The Benefit Of U.S. Provisional Application Ser. No. 61/098,578 Filed On Sep. 19, 2008. This Application is a Divisional Application of U.S. Formal application Ser. No. 12/563,658 Filed On Sep. 21, 2009

BACKGROUND OF THE INVENTION

1. Field of the Invention

This invention relates to a method and device for reducing muscle tension through electrical manipulation by applying a low level current to at least one muscle of a user. More particularly, this invention relates to a method and device for varying the frequency and intensity of the current being applied to a muscle during specific time periods pursuant to a predetermined program that is preferably selected from a group of programs prior to the commencement of the program. Each muscle has two electrodes applied thereto, one electrode passing the current from the device to the muscle and the other electrode receiving the current from the muscle to complete the circuit. The device can also be used to diagnose an ailment of a user.

2. Detailed Description of the Prior Art

A method and apparatus for strengthening skeletal muscles through maximizing muscle tension in which electrical stimulation signals are applied to the selected muscles at a predetermined frequency, pulse width, and amplitude is described in Lieber, U.S. Pat. No. 4,838,272 issued on Jun. 13, 1989. Electrical stimulation signals are applied to selected muscles at a predetermined frequency, pulse width, and amplitude to cause the muscles to contract and the work output by the muscles in response to the stimulation signals is determined over a fixed period of time. The work output is compared to a defined value, which can be a target value or a value measured during a previous stimulation period. The frequency or pulse width of stimulation signals applied to the muscles by the stimulation signals is varied in response to the results of the comparison between the work output and the defined value. The frequency is increased as the work increases and the frequency is decreased as the work decreases. The purpose of the invention described in the Lieber Patent is to increase muscle strength through long-term muscle work or activity. The output from the stimulation is transferred along the electrodes to the muscles.

The use of electrical pulses or signals to induce muscle contractions and thus stimulate muscle movement or exercise is described in the background of the Lieber U.S. Pat. No. 4,838,272 to stimulate muscle movement for paralyzed limbs or for individuals having various neurological or muscular disorders to motivate non-functional muscles. Also, when injuries occur, traditional exercise may not be possible and muscles can be strengthened to decrease the impact of injuries or surgery.

It is known to reduce muscle tension through manual massage and through the use of various pharmaceuticals. Massage requires many treatments and pharmaceuticals are not very effective and not site specific. Interferential current stimulation and transcutaneous electrical nerve stimulation is known to reduce muscle tension. However, both of these forms of stimulation result in contraction of the muscle producing fatigue and the fatigued muscle has a reduced level of muscle tension. However, a fatigued muscle is electrically and biochemically different from a relaxed muscle.

The Oldham U.S. Pat. No. 6,865,423 issued Mar. 8, 2005 describes a method for electrically stimulating a muscle and an electrical muscle stimulator. The stimulator produces a series of regularly spaced bursts of pulses with each burst, including a first component as a first continuous train of regularly spaced pulses, and second component as a series of regularly spaced second trains of regularly spaced pulses. The first component and the second component are combined and the spacing between successive pulses in the second pulse trains are less than the spacing between the successive pulses in the first pulse train. The method describes applying the stimulating signal to a muscle. The stimulation signal is applied through two electrodes, one electrode for each channel, to contract the muscle and the Patent states that it has long been established that the application of an electrical field to muscles results in an artificially induced contraction of the muscles. Each channel is coupled to one of the electrodes.

SUMMARY OF THE INVENTION

It is an object of the present invention to provide a method and device of applying a low level alternating current to muscles of a user, using a device having a controller to control a voltage of the device and a frequency and intensity of the current applied to one or more muscles of the user at a series of predetermined frequencies for predetermined times for each frequency. It is a further object of the present invention to have a controller in the device where the controller can be programmed and predetermined in advance for each user to apply a current to one or muscles through electrodes by a series of predetermined frequencies for predetermined times for each frequency. Preferably, the device has a plurality of circuits with a separate circuit being used for each muscle. Each circuit preferably has two electrodes, one of the two electrodes for passing current to a muscle and the other of two electrodes for receiving current from the muscle to complete the circuit. It is a further object of the present invention to provide a device and method for causing one or more muscles of a user to relax through electrical manipulation at a level below the threshold level that would cause the one or more muscles to contract.

It is a further object of the invention to provide a method and device that results in muscle relaxation through electrical manipulation at an intensity level below the threshold level at which a muscle will contract without producing muscle fatigue.

A method of relaxing muscle tension through electrical manipulation by applying a low level alternating current to muscles of a user is provided. The method uses a device having a power source and a controller to control a voltage and frequency of the alternating current applied to at least one muscle for a given period of time. The device has a plurality of electrodes and is programmed with at least one program. The method comprises connecting the device to a power source, connecting two electrodes of said plurality of electrodes to each muscle of said at least one muscle, activating the program for the device to apply to the at least one muscle of the user a low level alternating current at a series of predetermined frequencies in succession for predetermined times for each frequency, at a predetermined intensity of current for each frequency, applying two electrodes of the plurality of electrodes to each muscle of the at least one muscle, activating the device to carry out the program by passing the current through each muscle of the at least one muscle from one of the two electrodes of each muscle to the other of the two electrodes of each muscle, deactivating the device and removing the electrodes upon completion of the program.

A device for reducing muscle tension through electrical stimulation by applying a low level alternating current to at least one muscle of a user is provided. The device comprises a power source, a plurality of electrodes, two electrodes of the plurality of electrodes being in contact with each muscle that is being treated of the at least one muscle that is being treated of the user. One electrode on that muscle is connected to supply current to muscle, and another electrode on each muscle is connected to receive current from that muscle to complete a circuit from the device for each muscle being treated, there being a separate circuit for each muscle being treated. The electrodes on each muscle constitute a pair of electrodes. A controller controls a frequency and intensity of the alternating current for fixed periods of time and automatically varies the frequency and time for which a particular frequency and intensity of current is applied for each circuit. The intensity is adjustable by the controller prior to commencing a program of the device, the program applying the current at predetermined frequencies for predetermined times in succession for each circuit. The program is set for each user in advance of activating the program for that user. The intensity is capable of being set below a threshold of causing each muscle of the at least one muscle to contract.

A method of diagnosing ailments through electromanipulation by applying a low level alternating current to muscles of a user is provided. The method uses a device having a power source and a controller to control a voltage and frequency of the alternating current applied to at least one muscle for a given period of time. The device has a plurality of electrodes and the device is programmed. The method comprises connecting the device to the power source, connecting two of the plurality of electrodes to each muscle of said at least one muscle, activating the program for the device to apply to the at least one muscle a low level alternating current at a first frequency for a pre-determined time, using the controller to varying intensity of the low level current to each muscle of the at least one muscle to a level intensity that is slightly lower than a level required to cause the at least one muscle to contract or twitch and determining a voltage of the device at the level of intensity of the current for each muscle of the at least one muscle, using the voltage to diagnose the ailment of user by comparing the voltage to a range of voltages for normal muscles and determining whether the voltage is higher or lower than the range.

DETAILED DESCRIPTION OF A PREFERRED EMBODIMENT

Figure 1:
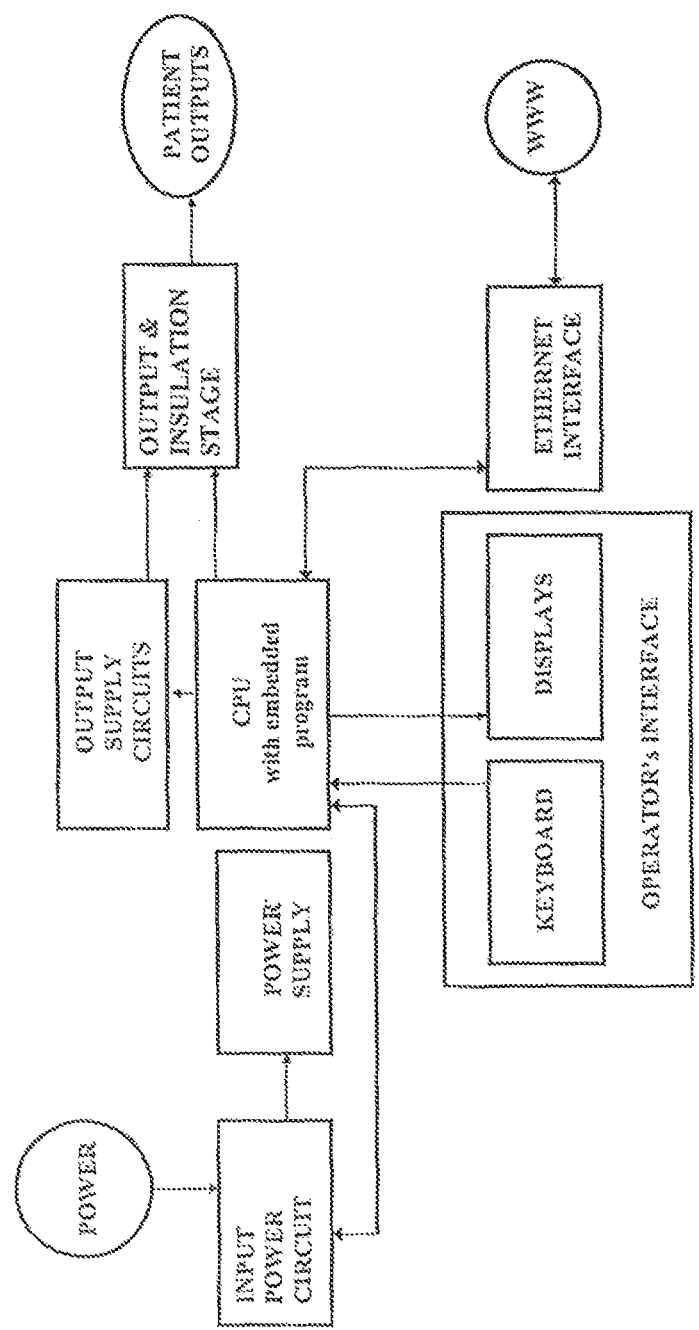
FIG. 1 is a block diagram showing the manner in which various components of the device are connected.

In FIG. 1, in a block diagram, it is shown that a device 100 for applying a low level current to at least one muscle of a user has an input power circuit 102 which is connected to a power supply 103 with an on/off switch 104 that is designated power. The input power circuit is connected to a central processing unit ("CPU") 106 with an embedded software program. The CPU 106 is connected to output supply circuits 108 and to an output and insulation stage 110. The output supply circuits 108 are also connected to the output and insulation stage 110 in parallel to the CPU 106. The output and insulation stage 110 is connected to patient outputs 112 or electrodes (not shown in FIG. 1). The CPU 106 is also connected to a keyboard 114, which enables an operator to input information or vary the parameters and to displays 116 which display the information that has been inputted and the progress of the process after it has been initiated. The CPU 106 can also be connected to an ethernet interface 118 which allows access to the world wide web 120 to allow remote monitoring and/or control of the device.

Figure 2:
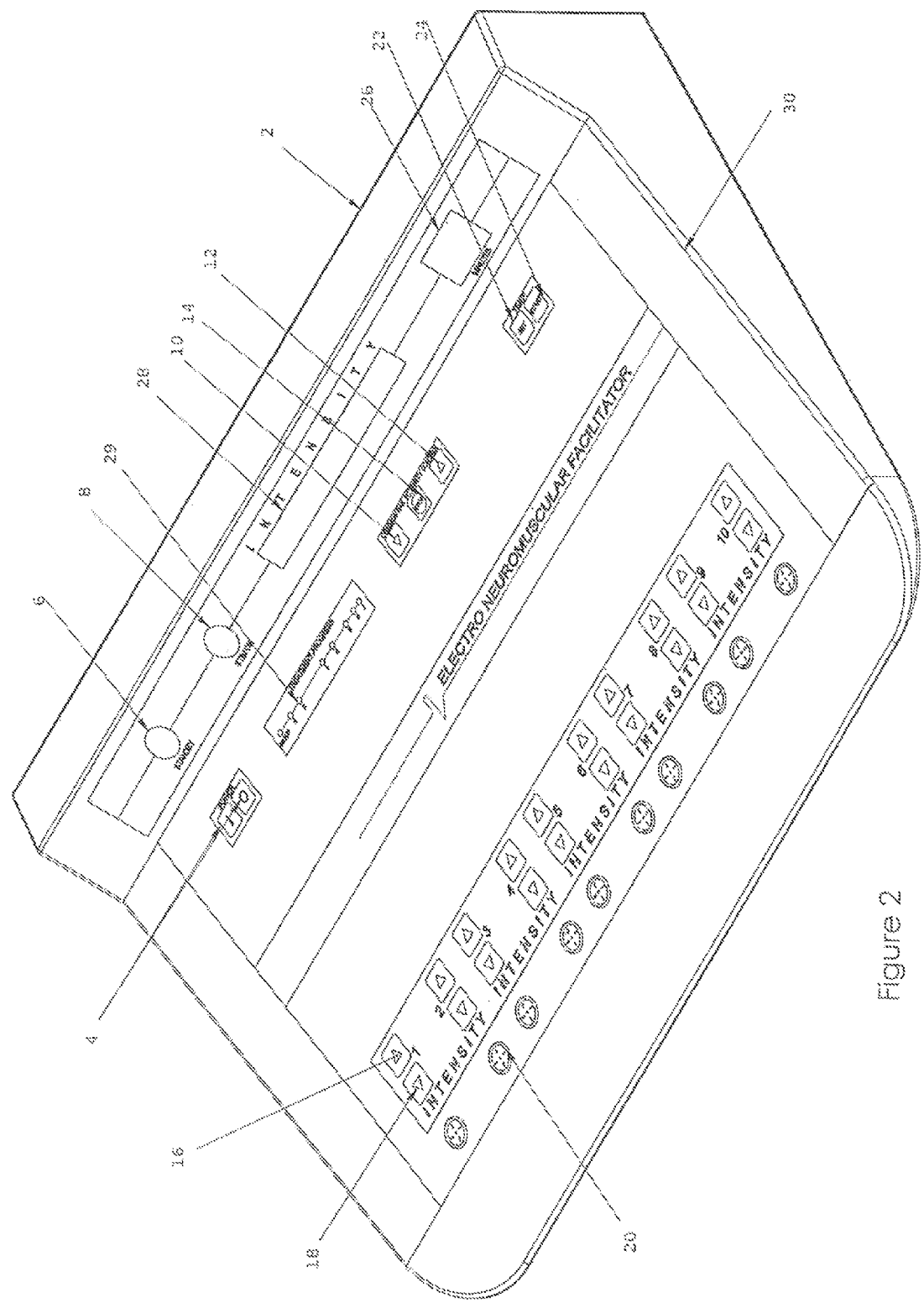
FIG. 2 is a perspective view of a front of a device for applying low level current.

In FIG. 2, there is shown a front view of a device 2 for applying low level current to muscles of a patient user. A power cord for connecting the device to an AC power source is not shown in FIG. 2 and is conventional. The device has an on/off switch 4 with a standby indicator lamp 6 and stimulator indicator lamp 8. There are intensity control buttons 10, 12 for decreasing or increasing respectively the current intensity to electrodes (not shown in FIG. 2). An indicator light 14 is located between the intensity control buttons 10, 12. Near the front of the device 2 are a series of intensity control buttons 16, 18 where the buttons 16 are depressed to increase intensity and the buttons 18 are depressed to decrease intensity. It will be noticed that each pair of buttons 16, 18 from left to right is numbered from 1 to 10 and represents a channel as there are ten pairs of buttons 16, 18. There is also a number of output sockets 20, with one socket being available for each pair of intensity control buttons 16, 18. A double wire (not shown) for each pair of electrodes (not shown) has a plug (not shown) at one end and two electrodes at the other end. One of the two wires is connected to each electrode and the plug is compatible with the sockets 20. On the right hand side of the device 2, there are timer setting buttons 22, 24 and a timer display 26. At the approximate center near the back of the device 2, there is a parameter and program display 28, which displays the inputs entered into the device for each patient user. Between the on/off switch 4 and the intensity control buttons 10, 12, there are located treatment progress indicator lamps 29 to show the progress of the program being carried out with respect to a patient. On the right hand side of the device 2, there is an ethernet connector socket 30.

Preferably, the device is programmed to apply the frequencies in 20 second bursts, with 0.5 seconds between bursts. There are preferably 20 second trains of electrical impulses at a particular frequency with a 0.5 second gap between each train. Preferably, the pulse width is of 200 microsecond duration and the wave form is rectangular in nature. The maximum voltage is preferably 70 volts with a peak at a resistance of 1 K ohm. Each train represents one frequency and trains are successive.

Figure 3:
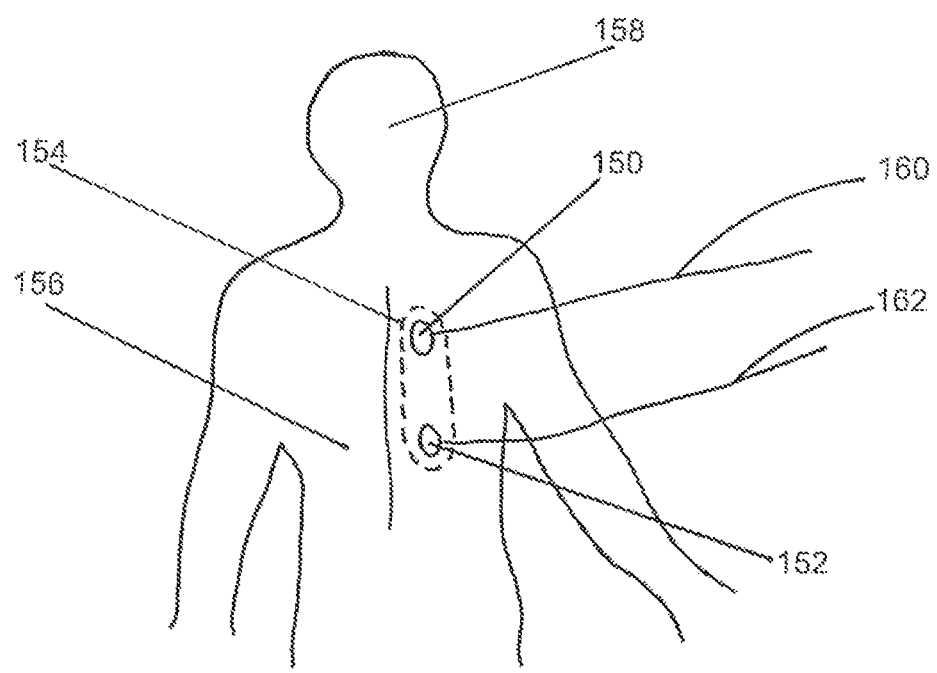
FIG. 3 is a schematic view of electrodes connected to a muscle on a back of a user.

In FIG. 3, electrodes 150, 152 are connected at either end of a muscle 154 (shown by way of dotted lines) on a back 156 of a user 158. The electrodes 150, 152 are connected by wires 160, 162 respectively to a device (not shown in FIG. 3) for applying low level current to the muscle 154 of the user in a manner that will relax the muscle 154 in accordance with the present invention.

In a method of operating the device, the power switch is turned on and the standby indicator light is illuminated. The electrodes, which have pads (not shown) are placed on the user with one electrode being placed at either end of the muscle to be treated. The user can more particularly be described as a patient. The electrodes are connected through the double wire assembly, as described above, to an output socket. When the device is removed from the standby mode and activated, and the electrodes (not shown) are in contact with a user, current flows from the device to a first electrode at one end of the muscle to be treated to a second electrode at the other end of the muscle to be treated and back to the device to complete the circuit. The electrode has conductive material located between the electrodes and the patient's body. This provides a buffer for the current to be applied to the muscle. The device can be used to treat more than one muscle at a time, and preferably when the muscle or muscles being treated are on one side of a patient's body, the same muscle or muscles on the other side of the patient will also be treated. For example, if the muscle on the right hand side of the patient is to be treated, the same muscle on the left hand side of the patient will be treated simultaneously even if the muscle on the left hand side is not causing any discomfort to the patient. The most important muscles to be treated on the back of a patient are located 1-2 cm lateral to the spinal processes.

After all the electrodes are secured to the patient, using straps, adhesive surfaces, suction cups or other means of securing the electrodes, the patient will move to a comfortable position, and will usually be asked to lie on the electrodes. If the electrodes are located on the patient's back, the patient will turn over after the electrodes have been placed, and lie on his/her back.

The operator of the device then chooses and sets the treatment time, preferably for substantially 30, 45, 60 or 90 minutes, as is deemed appropriate for a particular patient. When the treatment time has been selected, an operator then begins to set the intensity of the current for each of the electrode channels, there being one electrode channel for each muscle being treated. Each electrode channel is a separate circuit for the muscle that is being treated, each channel having two electrodes. The current applied by the device to a particular muscle flows from the device through one of the electrodes, through the muscle of the patient or user, and back to the device through the other electrode. It is important to set the intensity settings to a level just below the threshold for a muscle twitch or contraction for the muscle that is being treated. The operator increases the intensity of the current for the electrodes on the particular muscle to produce a mild twitch or mild contraction in the muscle and then slowly decreases the intensity of the current until only the sensation of the current is perceived by the patient, but there is no twitch or contraction feeling or any appearance of a twitch or contraction in the muscle. The contraction can be a tetanic or twitch contraction. Each of the electrodes is set to the same level of intensity for a particular muscle and the level of intensity is set for each of the muscles to be treated during the same treatment time below the threshold for each muscle that causes a contraction. For muscles that correspond to one another, the appropriate intensity level can be determined for one of the muscles, but must still be independently determined for the other corresponding muscle. The corresponding muscle is a muscle on one side of the body that corresponds to the same muscle on the other side of the body of the patient. When all of the electrodes are in place and the level of intensity has been established the operator proceeds to start the treatment by pressing the start button 24, which is the stimulation on lamp in FIG. 2.

At this time, the operator may record the percentage of intensity of each channel of the device for comparison to normative values and/or comparison to past or future intensity settings for that patient.

The program of the device will proceed through different frequencies at their proper time allotments automatically based upon the total program time chosen by the operator for that patient and inputted it into the device as stated above. The sequence of frequencies are predetermined and preferably pre-programmed into the device through a programmable controller. The preferred frequencies and the sequence thereof for a total treatment time of 30 minutes for each circuit is 80 hertz for 15 minutes, 4 hertz for 4 minutes, 30 hertz for 5 minutes, 50 hertz for 2 minutes, 80 hertz for 2 minutes and 120 hertz for 2 minutes. Still more preferably, the frequencies and the sequence thereof for a total treatment time of 30 minutes for each circuit is 80 hertz for 5 minutes, 120 hertz for 10 minutes, 4 hertz for 4 minutes, 30 hertz for 5 minutes, 50 hertz for 2 minutes, 80 hertz for 2 minutes and 120 hertz for 2 minutes. The times are preferred times, but other times are suitable as well.

When the treatment program is commenced, the operator should instruct the patient to signal the operator if they feel any pain or discomfort, or twitch or contraction in their muscles. The operator should be able to audibly monitor the patient during treatment and, if necessary, make adjustments to the intensity of the electrodes to ensure proper intensity levels are maintained throughout the treatment. In most cases, no adjustment will be required after the intensity level is set for each muscle before the program commences. When the treatment is completed, the machine will produce an audio signal and automatically shut down. The electrode pads are removed from the patient and arrangements are made for a subsequent treatment or treatments, if required. Most often, several treatments are required and the number of treatments usually ranges from 2 to 5, but each case must be considered independently and the number of treatments can vary widely. The sequence of frequencies and times set out above is for a 30 minute treatment program. When the treatment program is longer than 30 minutes, the times for each frequency increase proportionately. The factor is 1.5, 2 and 3 for 45 minutes, 60 minutes and 90 minutes respectively. When the treatment time is increased beyond thirty minutes, the device automatically increases the time at each frequency proportionally. While the exact frequencies and times set out in the sequence are preferred, substantially the same frequencies and times can also be used. A range of frequencies for the 30, 50, 80 and 120 hertz is ±5 hertz and the range for the 4 hertz frequency is ±2 hertz. The preferred ranges of frequency, in order of application are therefore 75 to 85 hertz, 115 to 125 hertz, 2 to 6 hertz, 25 to 35 hertz, 45 to 55 hertz, 75 to 85 hertz and 115 to 125 hertz. The treatment times are flexible and the time at each frequency is also flexible. Electrical impulses at 50 hertz and 80 hertz decrease the release of Leukotriene B4, a potent inflammatory substance. It is known that a muscle of shortened length cannot use the optimal compliment of acto-myosin bridges. The muscle therefore cannot generate as much muscle tension. A shortened muscle (caused by muscle tightness/spasm) does not regain full strength or endurance regardless of the strength and endurance exercises. A muscle in spasm or excessively tight, results in the release of several inflammatory compounds, including Leukotriene B4, due to the hypoxia that results from physical compression of the capillary beds. However, Leukotriene B4 reduces the blood flow in the muscle, resulting in the muscle fatiguing and tightening further, perpetuating the cycle. This perpetuating cycle of muscles fatiguing and tightening further can in some cases compress lymphatic vessels, causing an increase of fluid in the lymph vessel and the interstitial fluid also builds up. The result can be substantial swelling. This swelling can further compress the blood vessels causing the release of more Leukotriene B4 and this becomes a vicious circle. With the method and device of the present invention, muscles can be made to relax, without causing the muscles to contract during the program. The purpose of the device and method of the present invention is not to work the muscle(s), but to relax the muscle(s) of a user.

While the device and method of the present invention are particularly suited for lower back pain with the electrodes being in contact on either side of the back of the patient, the device and method can also be used to treat muscles and other parts of the body, for example, the arms and legs of a patient. For example, the method and device of the present invention can be used in the following therapeutic applications or ailments which are not intended to be exhaustive:

Muscle spasms (motor vehicle accident, occupational, personal injuries, stress)
    Repetitive strain injuries
    Carpal tunnel syndrome epicondylitis
    Bursitis,
    Tendonitis,
    Headaches
    Muscular,
    Vascular,
    Radiculopathies
    Frozen shoulder/thoracic outlet syndrome
    Trigeminal Neuralgia
    Temporal-Mandibular Joint Pain
    Multiple Sclerosis
    Parkinson's Disease
    Stroke Survivors
    Disc Injury or Degeneration
    Chronic Fatigue Syndrome
    Arthritis
    Osteoarthritis
    Rheumatoid
    Arteritis
    Polymyalgia
    Fibromyalgia
    Lupus The device and method of the present invention are effective in eliminating or reducing pain caused by injury or disease and is also effective in preventing further injury. The system results in relaxing the muscles treated. The process of the present invention relates generally to electrical manipulation of muscles for diagnostic purposes, rehabilitation therapy as well as treatment of specific diseases, conditions and injuries. The process of the present invention reduces the tension in specific muscles alleviating symptoms of the muscles to which it is applied. The process will allow for any nerve root compressions (when applied to paraspinal muscles), joint, vessel or other structures compressed by muscles to be released mitigating these results and dysfunctions, paraesthesias and/or pain symptoms. The invention can be used diagnostically as well as therapeutically.

For diagnostics concerning the skeletal muscles, in the first step of the method after the electrodes have been connected to apply low level alternating current to said at least one muscle in the first frequency range of 75-85 hertz and, preferably, at a frequency of 80 hertz, the device of the present invention can be used to determine the voltage that results in the device at that frequency (or range of frequencies) when the intensity of the current is set at a level that is slightly lower than a level required to cause the at least one muscle to contract or twitch. The other variables are the same as the initial settings for the therapeutic approach. At a frequency of 80 hertz, there is a narrow band of voltages that results in a maximum sub-threshold for contraction in healthy muscle tissue. This band of voltages ranges from 1.6 to 1.8 volts.

Voltage that is below the minimum voltage in the above range indicates a muscle that is hyper-sensitive as well as in spasm. Voltage that is higher than the maximum voltage in the above range indicates a muscle that is in very severe spasm. If the minimum threshold levels fall within the normal range, the muscle tissue is healthy and at most may require strength and endurance building. Therefore, the device of the present invention can be used to diagnose the location and the status of muscular problems that underlie various ailments including back pain, repetitive strain injuries, Multiple Sclerosis symptoms, Parkinson's Disease symptoms and Fibromyalgia among various other conditions.

The device increases the intensity level by increasing the current and the current is increased by increasing the voltage of the particular channel to which the electrodes are connected. Preferably, there is no overlap of frequencies and the frequencies of current are applied in succession.

Example 1

Electromanipulation of Muscles for the Treatment of Repetitive Strain Injury: A Pilot Study Aims:
The objective was to identify the efficacy of the protocol including the method and device of the present invention for patients suffering from pain in the forearm, wrist and hand caused by repetitive strain injury (RSI).

Method:
Seventeen volunteers participated in the study. Twelve females (mean age 41.5 plus or minus 9.9) and five males (mean age 35 plus or minus 8.7), followed the protocol for a minimum of six and a maximum of thirteen sessions (9.7 plus or minus 1.4) within one month. Subjects were excluded from this study if they presented with severe obesity (BMI >34.9) and/or pregnancy/All subjects followed the same protocol: electromyotherapy using the device and method of the present invention on specific muscles followed by a ten minute trigger point release and a protocol of stretches and strengthening for the neck and upper back muscles. The Board pain scale was used to acquire pain levels. Grip strength was measured using a hand dynamometer.

Results:
Pain levels were gathered before and after each session. For the purpose of this study, only data from the first (PTx1) and the last visit (PTxlas) was analyzed. Grip strength was measured prior to the first treatment (GTx1) and after the last visit (GTxlas). All data was analyzed using the One-way ANOVA and TUKEY'S post hoc comparisons. Results were statistically significant ($p<0.05$) for PTx1 and ($p=0.00$) for PTxlas. No significant differences was found for GTx1 and GTxlas ($p=0.12$).

Conclusion:
Preliminary data shows that perceived pain levels decreased after treatment following the above protocol for one month. This improvement leads to the conclusion that the protocol can be an efficient tool in the treatment of RSI.

Example 2

Electromanipulation of Muscles for the Treatment of Low Back Pain

Aims:
The objective was to identify the efficiency of the protocol including the method and device of the present invention for patients suffering from low back pain (LBP).

Method:

Fifteen volunteers participated in the study. Eight females (mean age 47.5 plus or minus 12.4) and seven males (mean age 41.8 plus or minus 13.0), followed the protocol for a minimum of four and maximum of ten sessions within two months. Volunteers were excluded from this study if they presented with neurological deficits in the legs due to a medical condition other than the back, severe obesity (BMI >34.9), severe spinal stenosis, Fibromyalgia and/or pregnancy. All subjects followed the same protocol: electromyotherapy using the device and method of the present invention on specific muscles followed by a ten minute trigger point release and a protocol of stretches and strengthening for the low back muscles. The Borg pain scale was used to acquire pain levels.

Results:

Pain levels were gathered prior to and after the first treatment (Tx1), fourth session (Tx4) and last visit (Txlas). All data was analyzed using One-way ANOVA. Results were statistically significant (p<0.05) when comparing pre and post for Tx1 (p=0.03) and Txlas (p=0.02). A significant difference was also found when comparing Tx1 to Tx4 (p=0.00), Tx4 to Txlas (p=0.00) and Tx1 to Txlas (p=0.00).

Conclusion:

Perceived pain levels were lower after subjects received their first treatment with the electrical manipulation in accordance with the present invention and significantly decreased after completion of the treatment plan. This improvement leads us to believe that the above protocol is an efficient tool in the treatment of LBP.

Example 3

A Physical Therapy Approach in the Treatment of Multiple Sclerosis

Aim:

To determine the efficacy of the protocol including the method and device of the present invention for patients suffering from MS of various types and durations.

Method:

Thirteen volunteers participated in this study, nine females (mean age 42.1 plus or minus 11.9) and four males (mean age 43.3 plus or minus 3.3). Volunteers were excluded if they presented with severe obesity (BMI>34.9), Fibromyalgia, severe spinal stenosis or pregnancy. All subjects followed the same protocol: electromyotherapy using the device and method of the present invention on specific muscles followed by a ten minute trigger point release and a program of stretching and strengthening the specific muscles. The participants received four to thirteen treatments within seven weeks. The Multiple Sclerosis Impact Scale (MSIS-29) was used to determine the degree of dysfunction at intake and completion. All data was analyzed using a One-way ANOVA.

Results:

All participant scores improved. The mean improvement was 25.6 plus or minus 18.4%. Participants demonstrated levels of individual improvement from 1.6% to 60.7% at completion. The results were statistically significant (p=0.03).

Conclusion:

The above protocol can be an effective physical therapeutic approach for treating MS of various types and durations.

We claim:

1. A method of relaxing muscle tension through electrical manipulation by applying a low level alternating current to a muscle of a user using a device having a power source and a controller to control a voltage and frequency of said alternating current applied to said muscle for a given period of time, said device having two electrodes that form a circuit, said device being programmed with at least one program, said method comprising connecting said two electrodes to said muscle, activating said device to cause said device to activate said program to apply to said muscle a low level alternating current at a series of predetermined frequencies in succession for predetermined times for each frequency at a predetermined intensity of current for each frequency, said device passing said current through said muscle from one of said two electrodes to the other of said two electrodes, deactivating said device and removing said electrodes upon completion of said program.

2. The method as claimed in claim 1, wherein prior to activating said program, setting said intensity at a level that is slightly lower than a level required to cause said muscle to contract or twitch.

3. The method as claimed in claim 2, wherein applying the series of frequencies to said muscle in the following sequence, within frequency ranges of 75-85 hertz for 15 minutes, 2-6 hertz for 4 minutes, 25-35 hertz for 5 minutes, 45-55 hertz for 2 minutes, 75-85 hertz for 2 minutes, and 115-125 hertz for 2 minutes, respectively, for a total of substantially 30 minutes.

4. The method as claimed in claim 3, wherein choosing a substantially constant frequency within each range.

5. The method as claimed in claim 3, wherein applying the series of frequencies to said muscle in the following sequence, substantially 80 hertz, 4 hertz, 30 hertz, 50 hertz, 80 hertz, and 120 hertz for times of substantially 15 minutes, 4 minutes, 5 minutes, 2 minutes, 2 minutes and 2 minutes, respectively, for a total of substantially 30 minutes.

6. The method as claimed in claim 2, wherein applying the series of frequencies to said muscle in the following sequence, within the frequency ranges of 75-85 hertz for 5 minutes, 115-125 hertz for 10 minutes, 2-6 hertz for 4 minutes, 25-35 hertz for 5 minutes, 45-55 hertz for 2 minutes, 75-85 hertz for 2 minutes, and 115-125 hertz for 2 minutes, respectively, for a total of substantially 30 minutes.

7. The method as claimed in claim 6, wherein choosing a substantially constant frequency within each range.

8. The method as claimed in claim 6, wherein applying the series of frequencies to said muscle in the following sequence, substantially 80 hertz, 120 hertz, 4 hertz, 30 hertz, 50 hertz, 80 hertz and 120 hertz for times of substantially 5 minutes, 10 minutes, 4 minutes, 5 minutes, 2 minutes, 2 minutes and 2 minutes, respectively, for a total of substantially 30 minutes.

9. The method as claimed in claim 1, wherein choosing six frequencies for said series of predetermined frequencies, and commencing with a first frequency that is substantially a second highest frequency of said series, dropping to a second frequency that is by far the lowest frequency of said series, increasing from said second frequency to a third frequency, from said third frequency to a fourth frequency, from said fourth frequency to a fifth frequency, and from said fifth frequency to a sixth frequency, where said fifth frequency is substantially the same as said first frequency.

10. The method as claimed in claim 1, wherein choosing seven frequencies for said series of predetermined frequencies, and commencing with a first frequency that is substantially a second highest frequency of said series, increasing to a second frequency that is higher than said first frequency, decreasing to a third frequency that is by far the lowest frequency of said series, increasing from said third frequency to a fourth frequency, from said fourth frequency to a fifth frequency, from said fifth frequency to a sixth frequency, and from said sixth frequency to a seventh frequency, where said sixth frequency is substantially the same as said first frequency, and said seventh frequency is substantially the same as said second frequency.

11. The method as claimed in claim 1, wherein ensuring that there is no overlap of said series of said frequencies.

12. The method as claimed in claim 2, wherein setting the said intensity for each muscle of said muscle to be treated.

13. The method as claimed in claim 2, wherein said muscle is a first muscle using said device on a second muscle on a back of a user, said first and second muscles being substantially symmetrical about a spine of said user and setting said intensity level for each of said first and second muscles.

14. The method as claimed in claim 3, wherein increasing said time for each frequency by a factor selected from the group of 1.5, 2 and 3 resulting in an increased total treatment time.

15. The method as claimed in claim 4, wherein increasing said time for each frequency by a factor selected from the group of 1.5, 2 and 3 resulting in an increased total treatment time.

16. The method as claimed in claim 5, wherein increasing said time for each frequency by a factor selected from the group of 1.5, 2 and 3 resulting in an increased total treatment time.

17. The method as claimed in claim 6, wherein increasing said time for each frequency by a factor selected from the group of 1.5, 2 and 3 resulting in an increased total treatment time.

18. The method as claimed in claim 1, wherein applying said current in a wave form that is rectangular and is applied from said device in 20 second bursts with 0.5 seconds between each burst.

19. A method as claimed in claim 1, wherein said two electrodes form a first circuit and said device has a plurality of channels, each channel having two electrodes and forming a separate circuit from the first channel, said muscle being a first muscle and said device being programmed with a plurality of programs, said method comprising operating said device to apply a low level alternating current to additional muscles to said first muscle of said user using one or more additional channels of said device and choosing a program for each muscle being treated from said plurality of programs, each channel being capable of operating a different program.

20. The method as claimed in claim 19 wherein prior to activating said program for said first muscle and any program for any additional muscles, setting said intensity for each muscle at a level that is slightly lower than the level required to cause each muscle to contract or twitch.

\* \* \* \* \*